United States Patent
Singh et al.

(10) Patent No.: US 11,174,563 B2
(45) Date of Patent: Nov. 16, 2021

(54) METHOD FOR TREATING SPENT CAUSTIC TO RECOVER CAUSTIC AND SULPHUR BY A BIOELECTROCHEMICAL PROCESS

(71) Applicant: INDIAN OIL CORPORATION LIMITED, Mumbai (IN)

(72) Inventors: Mahendara Pratap Singh, Faridabad (IN); Manoj Kumar, Faridabad (IN); Srikanth Sandipam, Faridabad (IN); Amardeep Singh, Faridabad (IN); Dheer Singh, Faridabad (IN); Umish Srivastava, Faridabad (IN); Suresh Kumar Puri, Faridabad (IN); Sanjiv Kumar Mazumdar, Faridabad (IN); Sankara Sri Venkata Ramakumar, Faridabad (IN)

(73) Assignee: INDIAN OIL CORPORATION LIMITED, Mumbai (IN)

( * ) Notice: Subject to any disclaimer, the term of this patent is extended or adjusted under 35 U.S.C. 154(b) by 373 days.

(21) Appl. No.: 16/147,724

(22) Filed: Sep. 29, 2018

(65) Prior Publication Data

US 2019/0119821 A1   Apr. 25, 2019

(30) Foreign Application Priority Data

Oct. 5, 2017 (IN) .............................. 201721035368

(51) Int. Cl.

| | |
|---|---|
| *C25B 9/23* | (2021.01) |
| *C02F 3/00* | (2006.01) |
| *C02F 3/34* | (2006.01) |
| *C25B 11/043* | (2021.01) |
| *C25B 11/057* | (2021.01) |
| *C12P 11/00* | (2006.01) |
| *C25B 1/16* | (2006.01) |
| *C02F 3/28* | (2006.01) |
| *C02F 101/10* | (2006.01) |
| *C02F 3/02* | (2006.01) |

(52) U.S. Cl.
CPC ................ *C25B 9/23* (2021.01); *C02F 3/005* (2013.01); *C02F 3/006* (2013.01); *C02F 3/341* (2013.01); *C12P 11/00* (2013.01); *C25B 1/16* (2013.01); *C25B 11/043* (2021.01); *C25B 11/057* (2021.01); *C02F 3/02* (2013.01); *C02F 3/2806* (2013.01); *C02F 2101/101* (2013.01); *C02F 2209/06* (2013.01)

(58) Field of Classification Search
None
See application file for complete search history.

(56) References Cited

U.S. PATENT DOCUMENTS

| | | | |
|---|---|---|---|
| 4,968,622 A | 11/1990 | Berzaczy et al. | |
| 5,480,550 A | 1/1996 | Sublette | |
| 6,045,695 A | 4/2000 | Janssen et al. | |
| 2001/0024351 A1 | 5/2001 | Berg et al. | |
| 2020/0102236 A1* | 4/2020 | Kumar ..................... | C02F 3/02 |

FOREIGN PATENT DOCUMENTS

IN   2480/MUM/2015   11/2017

OTHER PUBLICATIONS

Chen and Moris, "Kinetics of Oxidation of Aqueous Sulfide by Oxygen", Jun. 1972 Environmental Science and Technology vol. 6, No. 6, pp. 529-537.
Vaiopoulou et al., "Electrochemical sulfide removal and caustic recovery from spent caustic streams", Apr. 1, 2016, vol. 92, p. 38-43.
Buisman et al., "Optimization of sulphur production in a biotechnological sulphide-removing reactor", Biotechnology and Bioengineering vol. 35 pp. 50-56, Jan. 5, 1990.
Badr et al., "Biological removal of methanethiol from gas and water streams by using Thiobacillus thioparus: investigation of biodegradability and optimization of sulphur production". Environ Technol. Aug. 2014; 35(13-16):1729-35).
"A biological process for the treatment of spent caustics was described by Rajganesh", Sublette, Camp and Richardson, Biotechnology Progress, 1995 (11), 228-230.

* cited by examiner

*Primary Examiner* — Christian L Fronda
(74) *Attorney, Agent, or Firm* — Maschoff Brennan

(57) ABSTRACT

The present invention relates to an apparatus and method for bio-assisted treatment of spent caustic obtained from hydrocarbon and gas processing installations. The present invention also relates to method for recovery of caustic and recovery of sulfur from spent caustic. According to present invention, the sulfide removal is about 96% and the sulphur formation and deposition on the electrode lies in range of 72±8%.

14 Claims, 2 Drawing Sheets
Specification includes a Sequence Listing.

Two stage process where the stage-1 and stage-2 are performed in the same reactor for recovery of caustic and sulfur along with treatment of spent caustic

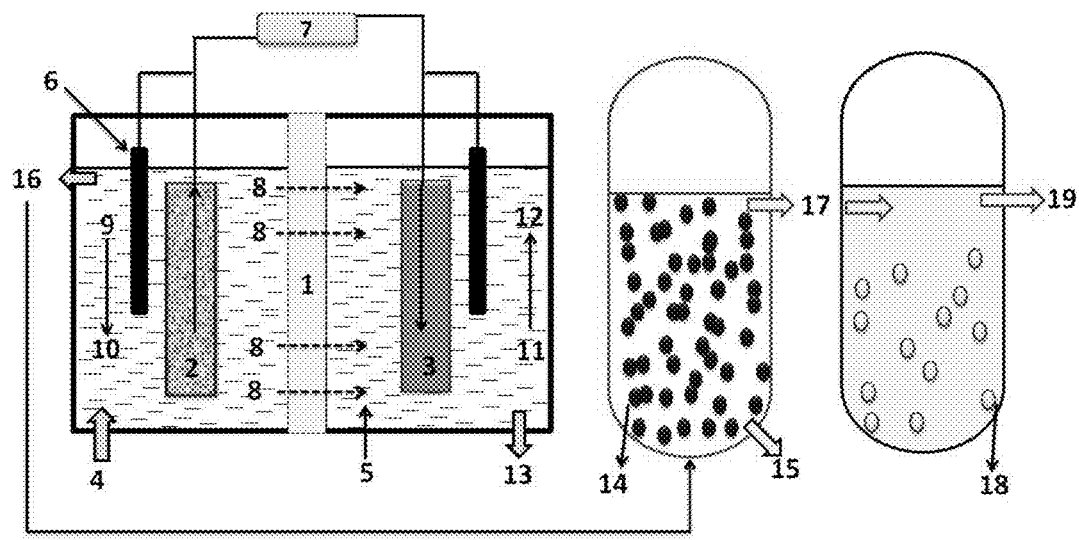
Figure 2:
Three stage process for recovery of caustic and sulfur along with treatment of spent caustic
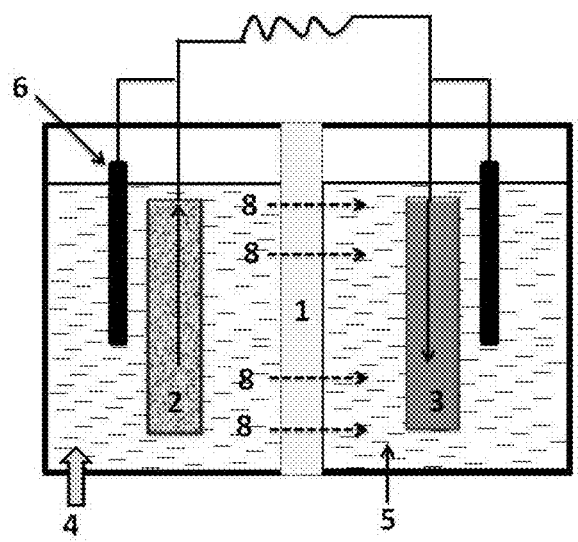
Figure 3: Control used in the present invention

SEQUENCE LISTING

<160> NUMBER OF SEQ ID NOS: 3

<210> SEQ ID NO 1
<211> LENGTH: 1497
<212> TYPE: DNA
<213> ORGANISM: Thiobacillus sp.

<400> SEQUENCE: 1

```
agagtttgat cctggctcag attgaacgct ggcggaatgc tttacacatg caagtcgaac      60
ggcagcacgg gagcttgctc ctggtggcga gaggcgaacg ggtgagtaat gcgtcggaac     120
gtaccgagta atgggggata acgcagcgaa agctgtgcta ataccgcata cgccccgagg     180
gggaaagcag gggatcgcaa gaccttgcgt tattcgagcg gccgacgtct gattagctag     240
ttggtggggt aaaggcctac caaggcgacg atcagtagcg ggtctgagag gatgatccgt     300
cacactggga ctgagacacg gcccagactc ctacgggagg cagcagtggg gaattttgga     360 caatggggc aaccctgatc cagccattcc gcgtgagtga agaaggcctt cgggttgtaa     420
agctctttca gaaggaacga aacggtacgc actaatattg tgtgctaatg acggtaccgg     480
cagaagaagc accggctaac tacgtgccag cagccgcggt aatacgtagg gtgcgagcgt     540
```

```
taatcggaat tactgggcgt aaagcgtgcg caggcggatt attaagcaag acgtgaaagc    600
cccgggctta acctgggaat ggcgttttga actggtagtc tagagtgtgt cagagggggg    660
tggaattcca cgtgtagcag tgaaatgcgt agatatgtgg aggaacacca atggcgaagg    720 cagcccctg ggataacact gacgctcatg tacgaaagcg tgggtagcaa gcaggattag     780
ataccctggt agtccacgcc ctaaacgatg tcaacaggtt gttggggag tgaaatccct     840 tagtaacgaa gctaacgcgt gaagctgacc gcctggggag tacggtcgca agattaaaac    900
tcaaaggaat tgacggggac cgcacaagc ggtggatgat gtggattaat tcgatgcaac     960
gcgaatcacc ttacctaccc ttgacatgtc cagaatcctg cagagatgcg ggagtgcccg   1020
aaagggaatt ggaacacagg tgctgcatgg gtgtcgtcag ctcgtgtcgt gagatgttgg   1080
gttaagtccc gtaacgagcg caacccttat cataagttgc tacgcaaggg cactctaatg   1140
agactgccgg tgacaaaccg gaggaaggtg gggatgacgt caagtcctca tggcccttat   1200
gggtagggct tcacacgtca tacaatggtc cgtacagagg gttgccaagc cgcgaggtgg   1260
agccaatccc agaaagccga tcgtagtccg gattgttctc tgcaactcga gagcatgaag   1320
tcggaatcgc tagtaatcgc ggatcagaat gccgcggtga atacgttccc gggtcttgta   1380
cacaccgccc gtcacaccat gggagtggaa tctgccagaa gtaggtagcc taaccgcaag   1440
gagggcgctt accacgttgg gtttcatgac tggggtgaag tcgtaacaag gtaacct       1497
```

<210> SEQ ID NO 2
<211> LENGTH: 1432
<212> TYPE: DNA
<213> ORGANISM: Thiomicrospira sp.

<400> SEQUENCE: 2

```
tctggcggya ggcttaacac atgcaagtcg gacggaaacg atagagaagc ttgcttatct    60
aggcgtcgag tggcggacgg gtgagtaacg cgtgggaatc taccctatag ttggggacaa   120
cgtatggaaa cgtacgctaa aaccgaatat gctctacgga gtaaaggagc cctcttcttg   180
aaaggtttcg ctataggatg agtccgcgta agattagcta gttggtaagg taatggctta   240
ccaaggcaac gatctttagc tggttttgaga ggatgatcag ccacactggg actgagacac   300
ggcccagact cctacgggag gcagcagtgg ggaatattgc acaatggacg aaagtctgat   360
gcagccatac cgcgtgtgtg aagaaggccc gagggttgta agcacattc aattgtgagg    420 aagatagwgt agttaatacc tgcwttgttt gacgttaact ttagaagaag caccggctaa   480
ctctgtgcca tcagccgcgg taatacgag ggtgcaagcg ttattcggaa ttactgggcg    540
taaagcgcgc gtaggcggat tattaagtca gttgtgaaag ccctgggctc aacctaggaa   600
ctgcatctga tagtggtaat ctagagttta ggagagggaa gtggaattcc aggtgtagca   660
gtgaaatgcg tagatatctg gaggaacatc agtggcgaag gccacttcct ggcctaaaac   720
tgacgctgag gtgcgaaagc gtgggtagcg aacgggatta gatacccgg tagtccacgc    780 cgtaaacgat gtcaactagt tgttggtcct attaaaagga ttagtaacga agctaacgcg   840
ataagttgac cgcctgggga gtacggtcgc aagattaaaa ctcaaaggaa ttgacggggg   900
cccgcacaag cggtggagca tgtggtttaa ttcgatgcaa cgcgaagaac cttaccatcc   960
cttgacatcc tgcgaacttt ctagagatag attggagcct tcgggaacgc agtgacaggt  1020
gctgcatggc tgtcgtcagc tcgtgtcgtg agatgttggg ttaagtcccg caacgagcgc  1080
aacccttatc aaaagttgct aacatttagt tgagaactgt aatgagactg ccggtgataa  1140
accggaggaa ggtggggacg acgtcaagtc atcatggccc ttatgggatg agctacacac  1200
```

-continued

```
gtgctacaat gggggtaca aagagctgcc aactggcaac agtgcgcgaa tctcaaaaaa    1260
cctctcgtag tccggatcgg agtctgcaac tcgactccgt gaagtcggaa tcgctagtaa    1320
tcgtggatca gaatgccgcg gtgaatacgt tcccgggcct tgtacacacc gcccgtcaca    1380
ccatgggagt ggattgcaaa agaagtaggt agcttaacct tcgggagggc tt           1432

<210> SEQ ID NO 3
<211> LENGTH: 1325
<212> TYPE: DNA
<213> ORGANISM: Pseudomonas putida

<400> SEQUENCE: 3
tggcggacgg gtgagtaatg cctaggaatc tgcctggtag tggggacaa cgtttcgaaa      60 ggaacgctaa taccgcatac gtcctacggg agaaagcagg ggaccttcgg gccttgcgct    120
atcagatgag cctaggtcgg attagctagt tggtgaggta atggctcacc aaggcgacga    180
tccgtaactg gtctgagagg atgatcagtc acactggaac tgagacacgg tccagactcc    240
tacgggaggc agcagtgggg aatattggac aatgggcgaa agcctgatcc agccatgccg    300
cgtgtgtgaa gaaggtcttc ggattgtaaa gcactttaag ttgggaggaa gggcagtaag    360 ctaataccttt gctgttttga cgttaccgac agaataagca ccggctaact ctgtgccagc    420
agccgcggta atacagaggg tgcaagcgtt aatcggaatt actttgcgta aagcgcgcgt    480
aggtggttcg ttaagttgga tgtgaaagcc ccgggctcaa cctgggaact gcatccaaaa    540
ctggcgagct agagtacggt agagggtggt ggaatttcct gtgtagcggt gaaatgcgta    600
gatataggaa ggaacaccag tggcgaaggc gaccacctgg actgatactg acactgaggt    660
gcgaaagcgt ggggagcaaa caggattaga taccctggta gtccacgccg taaacgatgt    720
caactagccg ttggaatcct tgagatttta gtggcgcagc taacgcatta agttgaccgc    780
ctggggagta cggccgcaag gttaaaactc aaatgaattg acggggggccc gcacaagcgg    840 tggagcatgt ggtttaattc gaagcaacgc gaagaacctt accaggcctt gacatgcaga    900
gaactttcca gagatggatt ggtgccttcg ggaactctga cacaggtgct gcatggctgt    960
cgtcagctcg tgtcgtgaga tgttgggtta agtcccgtaa cgagcgcaac ccttgtcctt   1020
agttaccagc acgttatggt gggcactcta gggagactgc cggtgacaaa ccggaggaag   1080
gtggggatga cgtcaagtca tcatggccct tacggcctgg gctacacacg tgctacaatg   1140
gtcggtacag agggttgcca agccgcgagg tggagctaat ctcacaaaac cgatcgtagt   1200
ccggatcgca gtctgcaact cgactgcgtg aagtcggaat cgctagtaat cgcgaatcag   1260
tatgtcgcgg tgaatacgtt cccgggcctt gtacacaccg cccgtcacaa ccatgggtag   1320
tgaaa                                                              1325
```

METHOD FOR TREATING SPENT CAUSTIC TO RECOVER CAUSTIC AND SULPHUR BY A BIOELECTROCHEMICAL PROCESS

FIELD OF THE INVENTION

The present invention relates to an apparatus and a method for bio-assisted treatment of spent caustic obtained from hydrocarbon and gas processing installations. The present invention also relates to method for recovery of caustic and recovery of sulfur from spent caustic.

The sequence listing disclosed herein is included in a text file having the name "I1609.10067US01_Sequence_Listing," created on Jan. 8, 2019, having a size of 7000 bytes. The foregoing text file is incorporated herein by reference.

BACKGROUND OF THE INVENTION

Aqueous sodium hydroxide solution is used for removal of sulfides, mercaptans and other sulfur compounds from gaseous and hydrocarbon streams in oil refinery processes. Once these contaminants come in contact and react with caustic solution, it cannot be further utilized and is known as spent caustic. The spent caustic contain un-utilized sodium hydroxide with contaminants like sulfides, mercaptans, amines, naphthenic acids, phenols, their derivatives, hydrocarbons and few other inorganic and organic compounds. Due to presence of these contaminants and high salinity and high pH, spent caustics are most difficult of all industrial wastes to dispose properly. Spent caustic is disposed by very expensive and environmentally reactive methods such as high dilutions and then treatment at ETP, deep well injections, incineration, wet air oxidation, humid hydrogen peroxide oxidation etc.

A biological process for the treatment of spent caustics was described by Rajganesh, Sublette, Camp and Richardson, Biotechnology Progress, 1995 (11), 228-230. In this process, sulfides are completely oxidized to sulfate by *Thiobacillus denitrificans*. This paper discloses a process which requires neutralization of spent caustic before treatment and only one impurity i.e, sulfides is removed.

U.S. Pat. No. 4,968,622 discloses a biological conversion process for degradation of sulfur-containing pollutants such as $H_2S$, $CS_2$, COS, and also organic surfur compounds such as thio-alcohols, thio-ethers, and thiophenes in waste gas. A packed reactor is provided which has packing material covered with immobilized microorganisms of the family of *Thiobacillus* and which are continuously kept moist, so that metabolic products of the microorganisms are dissolved in the moisture and discharged continuously. A continuous concentration gradient for sulfate ions thereby results in the reactor or in the region of the microorganisms, these sulfate ions being neutralized in a second reactor by supplying lye (soda or potash lye) forming readily-soluble salts.

Badr et al. (2014) (Biological removal of methanethiol from gas and water streams by using *Thiobacillus thioparus*: investigation of biodegradability and optimization of sulphur production. Environ Technol. 2014 August; 35(13-16): 1729-35) discusses biological oxidation of sulfides from gas and water streams by using *Thiobacillus thioparus*. In this process, methanethiol was converted into elemental sulphur particles as an intermediate in the oxidation process of MT to sulphate.

U.S. Pat. No. 5,480,550 discloses a biological process for the disposal for caustic waste streams containing inorganic sulfides to effect neutralization of the caustic and oxidation of sulfides to sulfates. The process disclosed in above said patent includes use of flocculated cultures of a sulfide-oxidizing bacterium from the genus *Thiobacillus* and various heterotrophs. The process includes immobilization of the bacteria and use of undefined mixture of microbes which are difficult to replicate. This process suffers from major drawback of immobilizing bacteria by co-culture with at least one floc-forming heterotroph under aerobic conditions to form a flocculated biomass. Secondly, the process of disposal of caustic waste streams is performed at pH of 7.0 and same is maintained by addition of 10N nitric acid solution. Hence, addition of heterotroph and nitric acid results into undesired addition of cost to the disposal process.

U.S. Pat. No. 6,045,695 discloses a process for the biological treatment of spent caustic solution containing sulfides, wherein the solution introduces into an aerobic reactor containing sulfide-oxidizing bacteria, and the sulfides are partly converted to elemental sulfur and partly to sulfate by controlling the redox potential in the reactor at a value below 300 mV (against an Ag/AgCl reference electrode), or below −97 (against reference electrode). The process suffers from disadvantages like the sulfide oxidation is done by using *M. sulfidovorans* which result into formation of thiosulfate. Usually thiosulfate is an undesirable component in waste water. Therefore, it is preferred then to combine the use of *M. sulfidovorans* with bacteria like genus *Thiobacillus* to convert thiosulfate to sulfate and/or sulfur which ultimately results into increase in the cost of disposal of impurities from spent caustic.

US 2001/0024351 discloses a method and apparatus for biologically treating a spent caustic to provide a treated spent caustic, said method comprising the steps of: (a) passing a spent caustic stream comprising water, alkali metal hydroxide and sulfide to a first bioreactor; (b) biologically oxidizing sulfide in the first bioreactor with sulfide-oxidizing bacteria like *thiobacillus* and *thiomicrospira*) to form sulfur and sulfate to provide a partially oxidized spent caustic; (c) passing the partially oxidized spent caustic to a second bioreactor where at least a portion of the partially oxidized spent caustic is further oxidized with sulfide-oxidizing bacteria to generate sulfate from sulfur to provide a treated spent caustic comprising sulfate. The drawbacks of above said process is that the process requires two bioreactors for treatment of spent caustic resulting into increase in cost. Further additional step of maintaining the pH to 8.5 is required wherein said pH is maintained by addition of acids like hydrochloric acid or sulfuric acid and hence results additional cost for chemical requirements. Moreover, only one impurity is treated like sulfides and therefore, additional process is required for the treatment of other impurities like phenols, amines, naphthenic acids, hydrocarbons etc. from spent caustic.

Buisman et al 1990 (Biotechnology and Bioengineering vol 35 pp 50-56, year 1990) discusses a biotechnological process for sulfide removal from H2S to elemental sulfur. The disclosed process works well at neutral pH.

Indian Patent Application No. 2480/MUM/2015 entitled "Bio-Assisted Process For Treatment And Regeneration Of Spent Caustic" discloses a bio-assisted method for treatment of spent caustic by treating with haloalkaliphilic consortium of bacteria capable of reducing or transforming sulfides, thiols, mercaptants and other sulphur containing compounds, phenols, hydrocarbons, naphthenic acids and their derivatives in spent caustic. In this process sulfides are completely oxidized to sulphate which contributes in increasing the TDS of the effluent.

Vaiopoulou and co-workers in 2016 (Eleni Vaiopoulou, Thomas Provijn, Antonin Prévoteau, Ilje Pikaar, Korneel Rabaey, Electrochemical sulfide removal and caustic recovery from spent caustic streams. 2016, 10.1016/j.watres.2016.01.039) reported the treatment of defined media simulating spent caustic stream (4 wt % NaOH and 1 wt % Na2S—S). They run the experiment abiotically under constant supply of high current densities (0-200 A/m$^2$) in galvanostat mode and studied different sulfide loading rates of 50-200 g(S)/L/d. They proposed that higher current densities support higher sulfide oxidation and more oxidized sulfur species will form but high loading rates of sulfide will result in a drop in sulfide oxidation efficiency. The said invention does not disclose methods of sulfur recovery since several oxidized sulfur species were present which were dominant than sulfur. In present invention, the real-field spent caustic for experimentation was used which apart from NaOH and Na2S, also contains, hydrocarbons, phenols and several other components. In the present invention, low voltages are used to recover the caustic and sulfur, which reduced the overall cost of the process significantly.

SUMMARY OF INVENTION

The present invention relates to an apparatus and method for bio-assisted treatment of spent caustic obtained from hydrocarbon and gas processing installations. The present invention also relates to method for recovery of caustic and recovery of sulfur from spent caustic. According to present invention, the sulfide removal is about 96% and the sulphur formation and deposition on the electrode lies in range of 72±8%.

In one of the embodiment, the present invention provides a method for treatment of spent caustic and recovery of caustic and sulphur by bioelectrochemical process, said process comprising the steps of:
(i) treating the spent caustic (4) in an electrochemical reactor comprising of two chambers separated by cation exchange membrane (1), electrode (2) wrapped with activated carbon cloth in first chamber and electrode (3) wrapped with noble metal in the second chamber, cations (8) present in the spent caustic are exchanged via cation exchange membrane (1) from first chamber to the second chamber, pH increases to 12-14 in the second chamber and associated pH drop of spent caustic is 7-9 in the first chamber, regenerating caustic and recovering caustic;
(ii) treating the spent caustic stream with lowered pH obtained from step (i) using a biocatalyst (14) for anaerobically oxidizing sulfides and other related compounds to elemental sulfur or its oxidized form; said biocatalyst (14) comprising one or more microbes selected from group comprising *Thiobacillus* sp., *Thiomicrospira* sp. and *Pseudomonas putida*; and
(iii) treating the spent caustic stream obtained from step (ii) using an aerobic biocatalyst (18) and obtaining a liquid with reduced concentration of sodium hydroxide, sulfides, amines, thiols, sulphur containing compounds, phenols, hydrocarbons, naphthenic acids and their derivatives; said biocatalyst (18) comprising one or more of *Pseudomonas putida* (MTCC 5385), *Pseudomonas aeruginosa* IOCX (MTCC 5389), *Bacillus* substilis (MTCC 5386), *Achromobacter* xylosoxidan IOC-SC-4 (MTCC 25024) *Pseudomonas stutzeri* (MTCC 25027), *Arthrobacter* sp. (MTCC 25028), *Bacillus subtilis* (MTCC 25026), *Achromobacter* xylooxidan (MTCC 25024).

In yet another embodiment, the present invention provides a method for treatment of spent caustic and recovery of caustic and sulphur as claimed in claim 1, wherein step (ii) is combined with step (i) and the biocatalyst (14) is present as biofilm on the electrode (2) in the first chamber of stage 1, anaerobically oxidizing sulphide and other related compounds to elemental sulfur (15) or its oxidized form by using biocatalyst (14) and recovers sulphur; and
feeding effluent (17) to subsequent stage reactor comprising aerobic biocatalyst (18) for treating effluent (17) and discharging completely treated effluent (19) with reduced concentration of sodium hydroxide, sulfides, amines, thiols, sulphur containing compounds, phenols, hydrocarbons, naphthenic acids and their derivatives.

In yet another embodiment, the present invention provides a method, wherein the microbes in biocatalyst (14) are used in adsorbed form or free form or immobilized on synthetic plastics, surface-modified carbon nanotubes, poly (tetrafluoroethylene) (PTFE) fibrils, zeolite, clay, anthracite, porous glass, activated charcoal, ceramics, acrylamide, polyurethane, polyvinyl, resins and natural polymer.

In yet another embodiment, the present invention provides a method, wherein the pH of second chamber increases and reaches to 12.68 and the associated pH drop of spent caustic is 7.08 in 12 hours.

In one of the another embodiment, the present invention provides a method 7, wherein the sulfide removal is about 96% and the sulphur formation and deposition on the electrode lies in range of 72±8%.

In one of the another embodiment, the present invention provides an apparatus for treatment of spent caustic and recovery of caustic and sulphur, said system comprising:
(i) an apparatus for stage 1 comprise of two chambers separated by cation exchange membrane (1),
first chamber receiving spent caustic (4) comprises electrode (2) wrapped with activated carbon cloth, a reference electrode (6) and connected to power supply (7);
second chamber receiving distilled water comprises electrode (3) wrapped with noble metal, a reference electrode (6) and connected to power supply (7);
the first chamber and second chamber are maintained at anaerobic condition, cations (8) present in the spent caustic are exchanged via cation exchange membrane (1) from first chamber to the second chamber, increases pH to 12-14 in second chamber and decreases the pH of anode to 7-9 in first chamber, and regenerates and recovers the caustic (13) in the second chamber;
(ii) an apparatus for stage 2 comprises biocatalyst (14), receives effluent from first chamber (16) with lowered pH from stage 1, anaerobically oxidize sulphide and other related compounds to elemental sulfur (15) or its oxidized form by using biocatalyst (14) and recovers sulphur; said biocatalyst (14) comprising one or more microbes selected from group comprising *Thiobacillus* sp., *Thiomicrospira* sp. and *Pseudomonas putida*; and
(iii) a reactor for stage 3 comprises aerobic biocatalyst (18), receives effluent (17) from stage 2 for treatment by the aerobic biocatalyst (18) and discharges completely treated effluent (19) with reduced concentration of sodium hydroxide, sulfides, amines, thiols, sulphur containing compounds, phenols, hydrocarbons, naphthenic acids and their derivatives; said biocatalyst (18) comprising one or more of *Pseudomonas putida* (MTCC 5385), *Pseudomonas aeruginosa* IOCX (MTCC 5389), *Bacillus* substilis (MTCC 5386), *Achromobacter* xylosoxidan IOC-SC-4 (MTCC 25024) *Pseudomonas stutzeri* (MTCC 25027), *Arthrobacter* sp. (MTCC 25028), *Bacillus subtilis* (MTCC 25026), *Achromobacter* xylooxidan (MTCC 25024).

In one of the another embodiment, the present invention provides an apparatus for treatment of spent caustic and recovery of caustic and sulphur, wherein stage 2 is combined with stage 1 and the biocatalyst (14) is present as biofilm on the electrode (2) in the first chamber of stage 1, anaerobically oxidize sulphide and other related compounds to elemental sulfur (15) or its oxidized form by using biocatalyst (14) and recovers sulphur; and effluent (17) is fed to subsequent stage reactor comprising aerobic biocatalyst (18) for treating effluent (17) and discharging completely treated effluent (19) with reduced concentration of sodium hydroxide, sulfides, amines, thiols, sulphur containing compounds, phenols, hydrocarbons, naphthenic acids and their derivatives.

In one of the another embodiment, the present invention provides an apparatus, wherein in stage 1, electrode (2) in first chamber comprises graphite rod, graphite plate, carbon brush, carbon paper, graphite felt; and electrode (3) in the second chamber comprises a carbon based electrode coated with noble metals, preferably graphite electrode (3) wrapped with stainless steel mesh.

In one of the another embodiment, the present invention provides an apparatus, wherein the sulfide removal is about 96% and the sulphur formation and deposition on the electrode lies in range of 72±8%.

BRIEF DESCRIPTION OF DRAWINGS

To further clarify advantages and aspects of the invention, a more particular description of the invention will be rendered by reference to specific embodiments thereof, which is illustrated in the appended drawings. It is appreciated that these drawings depict only typical embodiments of the invention and are therefore not to be considered limiting of its scope. The invention will be described and explained with additional specificity and detail with the accompanying drawings in accordance with various embodiments of the invention, wherein:

FIG. 2: Three-reactor configuration for recovery of caustic and sulfur along with treatment of spent caustic.

FIG. 3: Control experiment used in the present invention.

Figure 1:
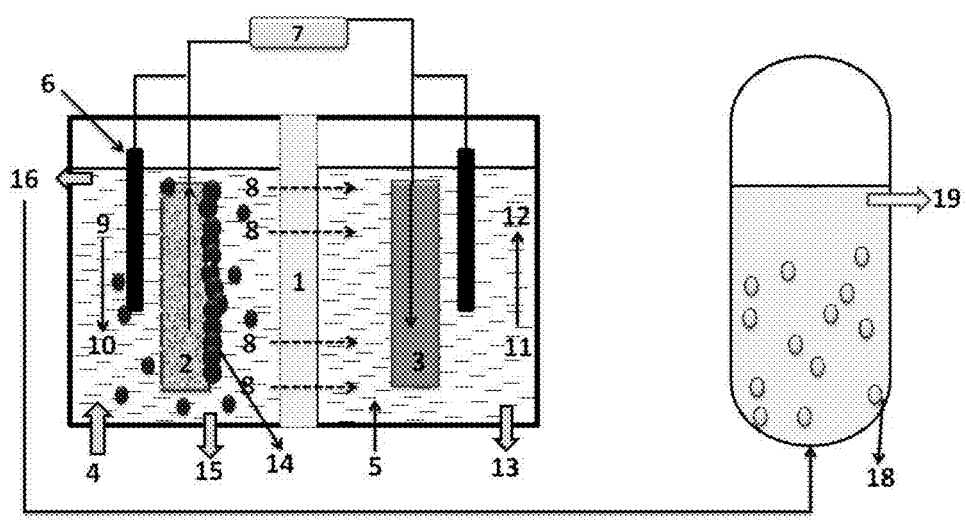
FIG. 1: Two-reactor configuration where the stage-1 and stage-2 are performed in the same reactor for recovery of caustic and sulfur along with treatment of spent caustic.

Furthermore, one or more elements may have been represented in the drawings by conventional symbols, and the drawings may show only those specific details that are pertinent to understanding the embodiments of the invention so as not to obscure the drawings with details that will be readily apparent to those of ordinary skill in the art having benefit of the description herein.

DETAILED DESCRIPTION OF THE INVENTION

While the invention is susceptible to various modifications and alternative forms, specific embodiment thereof will be described in detail below. It should be understood, however that it is not intended to limit the invention to the particular forms disclosed, but on the contrary, the invention is to cover all modifications, equivalents, and alternative falling within the scope of the invention as defined by the appended claims.

Although one or more features and/or elements may be described herein in the context of only a single embodiment, or alternatively in the context of more than one embodiment, or further alternatively in the context of all embodiments, the features and/or elements may instead be provided separately or in any appropriate combination or not at all. Conversely, any features and/or elements described in the context of separate embodiments may alternatively be realized as existing together in the context of a single embodiment.

The present invention relates to a system and method for bio-assisted treatment of spent caustic obtained from hydrocarbon and gas processing installations. The present invention also relates to method for recovery of caustic and recovery of sulfur from spent caustic.

The invention is explained with respect to the drawings accompanying this specification.

Two embodiments of using the inventive method of treating spent caustic are described in FIG. 1 and FIG. 2 along with control experiment as FIG. 3.

In accordance with the present invention, a three stage electro-bio-assisted assisted method of treating spent caustic is disclosed, said method comprising the steps of:

(i) treating the spent caustic (4) in an electrochemical reactor comprising of two chambers separated by cation exchange membrane (1), electrode (2) wrapped with activated carbon cloth in first chamber and electrode (3) wrapped with noble metal in the second chamber, cations (8) present in the spent caustic are exchanged via cation exchange membrane (1) from first chamber to the second chamber, pH increases to 12-14 in the second chamber and associated pH drop of spent caustic is 7-9 in the first chamber, regenerating caustic and recovering caustic;

(ii) treating the spent caustic stream with lowered pH obtained from step (i) using a biocatalyst (14) for anaerobically oxidizing sulfides and other related compounds to elemental sulfur or its oxidized form; said biocatalyst (14) comprising one or more microbes selected from group comprising *Thiobacillus* sp., *Thiomicrospira* sp. and *Pseudomonas putida*; and (iii) treating the spent caustic stream obtained from step (ii) using an aerobic biocatalyst (18) and obtaining a liquid with reduced concentration of sodium hydroxide, sulfides, amines, thiols, sulphur containing compounds, phenols, hydrocarbons, naphthenic acids and their derivatives; said biocatalyst (18) comprising one or more of *Pseudomonas putida* (MTCC 5385), *Pseudomonas aeruginosa* IOCX (MTCC 5389), *Bacillus* substilis (MTCC 5386), *Achromobacter* xylosoxidan IOC-SC-4 (MTCC 25024) *Pseudomonas stutzeri* (MTCC 25027), *Arthrobacter* sp. (MTCC 25028), *Bacillus subtilis* (MTCC 25026), *Achromobacter* xylooxidan (MTCC 25024).

In an embodiment of the present invention, apparatus for stage-1 comprise of two chambers separated by cation exchange membrane (CEM). One chamber is inserted with graphite rod wrapped with activated carbon cloth (ACC) and considered as working chamber where the spent caustic treatment occurs. The electrodes for this chamber can be varied, viz., graphite plate, carbon brush, carbon paper, graphite felt, etc. The other chamber is inserted with graphite electrode wrapped with stainless steel mesh (SS) and considered as counter chamber. The counter chamber may be of any carbon based electrodes coated with noble metals. One chamber having ACC electrode was fed with spent caustic, while the other chamber was fed with distilled water. The spent caustic chamber as well as counter chamber was maintained under anaerobic conditions. Both the chambers are equipped with Ag/AgCl (3M KCL) reference electrode. Both these electrodes will be connected through resistance or through power supply. The bioreactor can be operated at temperature ranging from 20–40° C. under constant applied voltage in the range of 0.1-5 V or current in the range of 5-250 A/m² vs Ag/AgCl reference electrode. The current can be provided from any renewable sources like solar or from electrical grid. The bioreactor can be operated in batch mode with a hydraulic retention time (HRT) of 5-48 h or in continuous mode with 2-24 h HRT. In continuous mode, spent caustic will fed to the working chamber at a flow rate of 1-20 ml/h and de-ionized water will fed to cathode at a flow rate of 1-25 ml/h.

In yet another embodiment of the present invention, the bioreactor in stage 2 of 3 stage process can be a suspended or packed column reactor having selective bacteria for sulfide oxidation to sulfur. The outlet from working chamber of stage-1 bioreactor having lowered pH (7-8) will be fed to this bioreactor and operated under anaerobic conditions. The packing material for the bioreactor can be gravel stones, polymeric material, sponge beads, etc. The bioreactor can be operated in batch mode with a HRT of 6-24 h or in continuous mode with 2-18 h HRT. Continuous mode operation can be at a flow rate of 5-50 ml/h. The bioreactor can be operated at temperature ranging from 25-45° C.

FIG. 2 represents three stage method for treatment of spent caustic and recovery of caustic and sulfur. The apparatus for stage-1 comprise of two chambers separated by cation exchange membrane (CEM) 1. One chamber is inserted with graphite rod wrapped with activated carbon cloth (ACC) 2 and considered as working chamber where the spent caustic treatment occurs. The electrodes for this chamber can be varied, viz., graphite plate, carbon brush, carbon paper, graphite felt, etc. The other chamber is inserted with graphite electrode wrapped with stainless steel mesh (SS) 3 and considered as counter chamber. The counter chamber may be of any carbon based electrodes coated with noble metals. One chamber having ACC electrode 1 was fed with spent caustic 4, while the other chamber was fed with distilled water 5. The spent caustic chamber as well as counter chamber was maintained under anaerobic conditions. Both the chambers are equipped with Ag/AgCl (3M KCL) reference electrode 6. Both these electrodes will be connected through resistance or through power supply 7. During stage-1 of treatment, the spent caustic 4 loaded to the working electrode chamber and distilled water to the counter electrode chamber. The cations 8 present in the spent caustic will be exchanged via the CEM 1 to the counter electrode chamber resulting in the lowering of pH 9 to 10. The exchanged cations from working chamber to the counter electrode chamber increase the pH of counter chamber from 11 to 12, regenerating the caustic 13, which can be recovered. However, there will be no biocatalyst present in the working chamber to enable the sulfur recovery in this approach. The effluent from working chamber 16 with lowered pH will be fed to the reactor in stage-2, where the selective biocatalyst 14 will anaerobically oxidize the sulfide to elemental sulfur 15 and recovered. The effluent 17 of stage-2 will be subjected to stage-3, where the aerobic biocatalyst 18 will be used for treating the remaining organic content and the completely treated effluent 19 will be discharged.

In an embodiment of the present invention, a two-reactor configuration is used in accordance with the invention, where the stage-1 and stage-2 are performed in the same reactor for recovery of caustic and sulfur along with treatment of spent caustic.

FIG. 1 represents the two stage method for treatment of spent caustic and recovery of caustic and sulfur. The apparatus for stage-1 comprise of two chambers separated by cation exchange membrane (CEM) 1. One chamber is inserted with graphite rod wrapped with activated carbon cloth (ACC) 2 and considered as working chamber where the spent caustic treatment occurs. The electrodes for this chamber can be varied, viz., graphite plate, carbon brush, carbon paper, graphite felt, etc. The other chamber is inserted with graphite electrode wrapped with stainless steel mesh (SS) 3 and considered as counter chamber. The counter chamber may be of any carbon based electrodes coated with noble metals. One chamber having ACC electrode 1 was fed with spent caustic 4, while the other chamber was fed with distilled water 5. The spent caustic chamber as well as counter chamber was maintained under anaerobic conditions. Both the chambers are equipped with Ag/AgCl (3M KCL) reference electrode 6. Both these electrodes will be connected through resistance or through power supply 7. During stage-1 of treatment, the spent caustic 4 loaded to the working electrode chamber and distilled water to the counter electrode chamber. The cations 8 present in the spent caustic will be exchanged via the CEM 1 to the counter electrode chamber resulting in the lowering of pH 9 to 10. The exchanged cations from working chamber to the counter electrode chamber increase the pH of counter chamber from 11 to 12, regenerating the caustic 13, which can be recovered. Simultaneously, the biocatalyst 14 present in working electrode chamber as biofilm on the electrode and in the suspension will anaerobically oxidize the sulfides present in the spent caustic converting them to elemental sulfur 15, which can be recovered. The effluent from working chamber 16 with low sulfide content and lowered pH will be fed to the reactor in stage-2, where the aerobic biocatalyst 18 will be used for treating the remaining organic content and the completely treated effluent 19 will be discharged.

In yet another embodiment of the present invention, the bioreactor in stage-3 for treating the left over contaminants such as hydrocarbons and phenols will in suspended mode added with aerobic bacteria. The outlet from the sulfur recovery bioreactor will be fed to this bioreactor and operated under aerobic conditions. The bioreactor can be operated in batch mode with a HRT of 2-18 h or in continuous mode with 2-10 h HRT. Continuous mode operation can be at a flow rate of 5-50 ml/h. The bioreactor can be operated at temperature ranging from 25–45° C.

In yet another embodiment of the present invention, the electrochemical treatment will result in regeneration of caustic at cathode and to increase its pH to 12-14 and decrease the pH of anode to 7-9. In accordance with the present invention treatment is done in batch mode as well as continuous mode using continuously stirrer reactor, up-flow reactor and such suitable reactor. In an embodiment of the present invention, the method of treatment of spent caustic can be used for recovery of sodium hydroxide from the spent caustic. In accordance with the present invention, the method of treatment of spent caustic can be used for recovery of elemental sulfur from the spent caustic.

In an embodiment of the present invention, the spent caustic treated in stage-2 is treated using a microbial consortia in stage 3 which resulted in reduced concentration of sulfides, amines, thiols, other sulphur containing compounds, phenols, hydrocarbons, naphthenic acids and their derivatives at least by 90%.

In accordance with the present invention the said microbes which can be used in stage 2 includes, but not limited to, *Thiobacillus* sp, *Thiomicrospira* sp, *Pseudomonas putida*, alone or in combination with each other. The representative species of the biocatalyst (14) are publically available in the depositories and are not claimed by the applicant. All species of these genus will perform the function, however the isolates may be characterized for following features:

*Thiobacillus:*
Gram staining: Negative
Colony morphology on thiosulphate-gellan gum plate: White to whitish yellow, cloud like shape
Motility: Positive
Growth on glucose, methanol, pyruvate: Negative
Iron oxidation: Negative
Nitrate respiration: Negative
Catalase: Positive
Oxidase: Positive
Thiocynate oxidation: Positive
More 99% homology with following sequences:

>*Thiobacillus* sp. 16S ribosomal RNA gene
(SEQ ID NO: 1)
AGAGTTTGATCCTGGCTCAGATTGAACGCTGGCGGAATGCTTTACACATG

CAAGTCGAACGGCAGCACGG

GAGCTTGCTCCTGGTGGCGAGAGGCGAACGGGTGAGTAATGCGTCGGAAC

GTACCGAGTAATGGGGGATA

ACGCAGCGAAAGCTGTGCTAATACCGCATACGCCCCGAGGGGGAAAGCAG

GGGATCGCAAGACCTTGCGT

TATTCGAGCGGCCGACGTCTGATTAGCTAGTTGGTGGGGTAAAGGCCTAC

CAAGGCGACGATCAGTAGCG

GGTCTGAGAGGATGATCCGTCACACTGGGACTGAGACACGGCCCAGACTC

CTACGGGAGGCAGCAGTGGG

GAATTTTGGACAATGGGGGCAACCCTGATCCAGCCATTCCGCGTGAGTGA

AGAAGGCCTTCGGGTTGTAA

AGCTCTTTCAGAAGGAACGAAACGGTACGCACTAATATTGTGTGCTAATG

ACGGTACCGGCAGAAGAAGC

ACCGGCTAACTACGTGCCAGCAGCCGCGGTAATACGTAGGGTGCGAGCGT

TAATCGGAATTACTGGGCGT

AAAGCGTGCGCAGGCGGATTATTAAGCAAGACGTGAAAGCCCCGGGCTTA

ACCTGGGAATGGCGTTTTGA

ACTGGTAGTCTAGAGTGTGTCAGAGGGGGTGGAATTCCACGTGTAGCAG

TGAAATGCGTAGATATGTGG

AGGAACACCAATGGCGAAGGCAGCCCCCTGGGATAACACTGACGCTCATG

TACGAAAGCGTGGGTAGCAA

GCAGGATTAGATACCCTGGTAGTCCACGCCCTAAACGATGTCAACAGGTT

GTTGGGGGAGTGAAATCCCT

TAGTAACGAAGCTAACGCGTGAAGCTGACCGCCTGGGGAGTACGGTCGCA

AGATTAAAACTCAAAGGAAT

TGACGGGACCCGCACAAGCGGTGGATGATGTGGATTAATTCGATGCAAC

GCGAATCACCTTACCTACCC

TTGACATGTCCAGAATCCTGCAGAGATGCGGGAGTGCCCGAAAGGGAATT

GGAACACAGGTGCTGCATGG

GTGTCGTCAGCTCGTGTCGTGAGATGTTGGGTTAAGTCCCGTAACGAGCG

CAACCCTTATCATAAGTTGC

TACGCAAGGGCACTCTAATGAGACTGCCGGTGACAAACCGGAGGAAGGTG

GGGATGACGTCAAGTCCTCA

TGGCCCTTATGGGTAGGGCTTCACACGTCATACAATGGTCCGTACAGAGG

GTTGCCAAGCCGCGAGGTGG

AGCCAATCCCAGAAAGCCGATCGTAGTCCGGATTGTTCTCTGCAACTCGA

GAGCATGAAGTCGGAATCGC

TAGTAATCGCGGATCAGAATGCCGCGGTGAATACGTTCCCGGGTCTTGTA

CACACCGCCCGTCACACCAT

GGGAGTGGAATCTGCCAGAAGTAGGTAGCCTAACCGCAAGGAGGGCGCTT

ACCACGTTGGGTTTCATGAC

TGGGGTGAAGTCGTAACAAGGTAACCT

Example

The example of such microbe are, but not limited to DSM 12475, DSM 5368, DSM 505, DSM 19892, DSM 700, DSM 3134, ATCC 25259, ATCC 23648, ATCC 8158 etc.

*Thiomicrospira* sp.
Gram staining: Negative
Cells: motile and rod-shaped
Colony morphology on thiosulfate agar, cells produce yellow, smooth, entire colonies
Motility: Positive
Growth on glucose, methanol, pyruvate: Negative
Catalase: Positive
Oxidase: Positive
Thiocynate oxidation: Negative
More 99% homology with following sequences:

>*Thiomicrospira* sp. 16S rRNA gene
(SEQ ID NO: 2)
TCTGGCGGYAGGCTTAACACATGCAAGTCGGACGGAAACGATAGAGAAGC

TTGCTTATCTAGGCGTCGAG

TGGCGGACGGGTGAGTAACGCGTGGGAATCTACCCTATAGTTGGGGACAA

CGTATGGAAACGTACGCTAA

AACCGAATATGCTCTACGGAGTAAAGGAGCCCTCTTCTTGAAAGGTTTCG

CTATAGGATGAGTCCGCGTA

AGATTAGCTAGTTGGTAAGGTAATGGCTTACCAAGGCAACGATCTTTAGC

TGGTTTGAGAGGATGATCAG

CCACACTGGGACTGAGACACGGCCCAGACTCCTACGGGAGGCAGCAGTGG

GGAATATTGCACAATGGACG

AAAGTCTGATGCAGCCATACCGCGTGTGTGAAGAAGGCCCGAGGGTTGTA

AAGCACATTCAATTGTGAGG

AAGATAGWTAGTTAATACCTGCWTTGTTTGACGTTAACTTTAGAAGAAG

CACCGGCTAACTCTGTGCCA

-continued
```
TCAGCCGCGGTAATACAGAGGGTGCAAGCGTTATTCGGAATTACTGGGCG

TAAAGCGCGCGTAGGCGGAT

TATTAAGTCAGTTGTGAAAGCCCTGGGCTCAACCTAGGAACTGCATCTGA

TAGTGGTAATCTAGAGTTTA

GGAGAGGGAAGTGGAATTCCAGGTGTAGCAGTGAAATGCGTAGATATCTG

GAGGAACATCAGTGGCGAAG

GCCACTTCCTGGCCTAAAACTGACGCTGAGGTGCGAAAGCGTGGGTAGCG

AACGGGATTAGATACCCCGG

TAGTCCACGCCGTAAACGATGTCAACTAGTTGTTGGTCCTATTAAAAGGA

TTAGTAACGAAGCTAACGCG

ATAAGTTGACCGCCTGGGGAGTACGGTCGCAAGATTAAAACTCAAAGGAA

TTGACGGGGCCCGCACAAG

CGGTGGAGCATGTGGTTTAATTCGATGCAACGCGAAGAACCTTACCATCC

CTTGACATCCTGCGAACTTT

CTAGAGATAGATTGGAGCCTTCGGGAACGCAGTGACAGGTGCTGCATGGC

TGTCGTCAGCTCGTGTCGTG

AGATGTTGGGTTAAGTCCCGCAACGAGCGCAACCCTTATCAAAAGTTGCT

AACATTTAGTTGAGAACTGT

AATGAGACTGCCGGTGATAAACCGGAGGAAGGTGGGGACGACGTCAAGTC

ATCATGGCCCTTATGGGATG

AGCTACACACGTGCTACAATGGGGGGTACAAAGAGCTGCCAACTGGCAAC

AGTGCGCGAATCTCAAAAAA

CCTCTCGTAGTCCGGATCGGAGTCTGCAACTCGACTCCGTGAAGTCGGAA

TCGCTAGTAATCGTGGATCA

GAATGCCGCGGTGAATACGTTCCCGGGCCTTGTACACACCGCCCGTCACA

CCATGGGAGTGGATTGCAAA

AGAAGTAGGTAGCTTAACCTTCGGGAGGGCTT
```

Example

The example of such microbe are, but not limited to ATCC 700954 DSM13453, ATCC 700955, DSM13458, DSM 1534, DSM 12351, DSM 12352, ATCC 35932, ATCC 700877, ATCC 49871, DSM: 12353, DSM: 13229.

Pseudomonas putida
Gram Negative
Catalase Positive
Oxidase Positive
Arginine dihydrolase: Positive
Gelatin: Negative
Urease: Negative
Nicotinate: Negative

```
>Pseudomonas putida strain 16S ribosomal RNA gene
                                      (SEQ ID NO: 3)
TGGCGGACGGGTGAGTAATGCCTAGGAATCTGCCTGGTAGTGGGGGACAA

CGTTTCGAAAGGAACGCTAA

TACCGCATACGTCCTACGGGAGAAAGCAGGGGACCTTCGGGCCTTGCGCT

ATCAGATGAGCCTAGGTCGG

ATTAGCTAGTTGGTGAGGTAATGGCTCACCAAGGCGACGATCCGTAACTG

GTCTGAGAGGATGATCAGTC

ACACTGGAACTGAGACACGGTCCAGACTCCTACGGGAGGCAGCAGTGGGG

AATATTGGACAATGGGCGAA

AGCCTGATCCAGCCATGCCGCGTGTGTGAAGAAGGTCTTCGGATTGTAAA

GCACTTTAAGTTGGGAGGAA

GGGCAGTAAGCTAATACCTTGCTGTTTTGACGTTACCGACAGAATAAGCA

CCGGCTAACTCTGTGCCAGC

AGCCGCGGTAATACAGAGGGTGCAAGCGTTAATCGGAATTACTTTGCGTA

AAGCGCGCGTAGGTGGTTCG

TTAAGTTGGATGTGAAAGCCCCGGGCTCAACCTGGGAACTGCATCCAAAA

CTGGCGAGCTAGAGTACGGT

AGAGGGTGGTGGAATTTCCTGTGTAGCGGTGAAATGCGTAGATATAGGAA

GGAACACCAGTGGCGAAGGC

GACCACCTGGACTGATACTGACACTGAGGTGCGAAAGCGTGGGGAGCAAA

CAGGATTAGATACCCTGGTA

GTCCACGCCGTAAACGATGTCAACTAGCCGTTGGAATCCTTGAGATTTTA

GTGGCGCAGCTAACGCATTA

AGTTGACCGCCTGGGGAGTACGGCCGCAAGGTTAAAACTCAAATGAATTG

ACGGGGGCCCGCACAAGCGG

TGGAGCATGTGGTTTAATTCGAAGCAACGCGAAGAACCTTACCAGGCCTT

GACATGCAGAGAACTTTCCA

GAGATGGATTGGTGCCTTCGGGAACTCTGACACAGGTGCTGCATGGCTGT

CGTCAGCTCGTGTCGTGAGA

TGTTGGGTTAAGTCCCGTAACGAGCGCAACCCTTGTCCTTAGTTACCAGC

ACGTTATGGTGGGCACTCTA

GGGAGACTGCCGGTGACAAACCGGAGGAAGGTGGGGATGACGTCAAGTCA

TCATGGCCCTTACGGCCTGG

GCTACACACGTGCTACAATGGTCGGTACAGAGGGTTGCCAAGCCGCGAGG

TGGAGCTAATCTCACAAAAC

CGATCGTAGTCCGGATCGCAGTCTGCAACTCGACTGCGTGAAGTCGGAAT

CGCTAGTAATCGCGAATCAG

TATGTCGCGGTGAATACGTTCCCGGGCCTTGTACACACCGCCCGTCACAA

CCATGGGTAGTGAAA
```

Example

The example of such microbe are, but not limited to Pseudomonas putida MTCC 5388, Pseudomonas putida MTCC 5387.

The microbes used at stage 2 also can be used in adsorbed form or in free form. The bacteria can be immobilized on synthetic plastics, surface-modified carbon nanotubes, poly (tetrafluoroethylene) (PTFE) fibrils, zeolite, clay, anthracite, porous glass, activated charcoal, ceramics, acrylamide, polyurethane, polyvinyl, resins and natural polymer etc. The advantage of the process based on immobilized biomass include enhancing microbial cell stability, allowing continuous process operation and avoiding the biomass—liquid separation requirement. The immobilization can be done as per the method known in prior art.

In yet another embodiment of the present invention, the method of the stage 2 of treatment of spent caustic use a nutrient system consisting of $K_2HPO_4$ (2-10 g/l), $KH_2PO_4$ (2-15 g/l), $MgCl_2$ (0.1-5 g/l), 0.5-2 ml trace elements, sodium carbonate (1-20 g/l), yeast extract (2-10 g/l), ammonium nitrate (3-7 g/l), citrate (1-20 g/l), Oleic acid (10-1000 ppm), pantothenic acid (2-500 ppm), thiamine (2.5-200 ppm). The trace element solution (gram per liter) comprises nitrilotriacetic acid (1.5), $FeSO_4.7H_2$ (0.05), $MnCl_2.4H_2O$ (0.015), $CoCl_2.6H_2O$ (0.09), $CaCl_2.2H_2O$ (0.50), $ZnCl_2$ (0.50), $CuCl_2.H_2O$ (0.03), $H_3BO_3$ (0.02), $Na_2MoO_4$ (0.02).

In yet another embodiment of the present invention, bioreactor having electrode pair was used in stage-1 followed by bioreactor s with selective microbial consortia in stage-2 and stage-3.

Another embodiment of the present invention relates to the microbes used in stage 2 which can work in pH range 7-9 and oxidized sulfides to elemental sulphur and sulphate where elemental sulphur form is at least 60%.

In yet another embodiment of the present invention, the spent caustic treated in stage-2 is treated using a microbial consortia in stage 3 which resulted in reduced concentration of sulfides, amines, thiols, other sulphur containing compounds, phenols, hydrocarbons, naphthenic acids and their derivatives at least by 90%.

In yet another embodiment of the present invention the consortia of bacteria used in stage 3 include *Pseudomonas putida* (MTCC 5385), *Pseudomonas aeruginosa* IOCX (MTCC 5389), *Bacillus* substilis (MTCC 5386), *Achromobacter* xylosoxidan IOC-SC-4 (MTCC 25024) *Pseudomonas stutzeri* (MTCC 25027), *Arthrobacter* sp. (MTCC 25028), *Bacillus subtilis* (MTCC 25026), *Achromobacter* xylooxidan (MTCC 25024).

| S. No. | Name of microbe | Short Description |
|---|---|---|
| 1 | *Pseudomonas putida* (MTCC 5385) | Gram-negative, rod-shaped, Catalase: +,Cytochrome C oxidase: +,Lecithinase/alpha: −; Casein hydrolysis: −,D-trehalose: −,Poly-β-hydroxybutyric acid: + Extracellular electron acceptor |
| 2 | *Pseudomonas aeruginosa* IOCX (MTCC 5389) | Gram-negative, rod-shaped, non-spore-forming elecroactive bacterium. Oxidase test-Positive, indole negative, methyl red negative, Voges-Proskauer test Positive and citrate positive. |
| 3 | *Bacillus substilis* (MTCC 5386) | Gram-positive spore forming motile bacterium, catalase-positive, Oxidase -Positive, Indole- Negative, Citrate Negative, Voges-Proskauer-Positive, Protease- Positive, Gelatinase-Negative, MR (Methyl Red)- Negative, Urease-Negative |
| 4 | *Achromobacter xylosoxida* IOC-SC-4 (MTCC 25024) | Ccatalase- and oxidase-positive, motile, Gram-negative rod that oxidizes xylose and glucose. citrate-positive. Urease and indole-negative Electroactive in nature. |

| S. No. | Name of microbe | Short Description |
|---|---|---|
| 5 | *Pseudomonas stutzeri* (MTCC 25027) | Gram-negative, rod-shaped, non-spore-forming bacterium. Positive for both the catalase and oxidase tests Electroactive in nature. |
| 6 | *Arthobacter* sp. (MTCC 25028) | Irregular-shaped Gram-negative rods changing to Gram-positive coccoid cells on further incubation; aerobic; liquefying gelatine slowly, chemo-organotrophs; catalase positive; oxidase positive. Starch Hydrolysis Test: positive, Casein Hydrolysis Test: positive, Gelatin Hydrolysis Test: negative, DNA Hydrolysis Test: negative Lipid Hydrolysis Test: positive, Methyl Red Test: negative, Voges Proskauer Test: negative, Citrate Test: negative |
| 7 | *Bacillus subtilis* (MTCC 25026) | Gram-positive spore forming motile bacterium, catalase-positive, Oxidase -Positive, Indole- Negative, Citrate Negative, Voges-Proskauer-Positive, Protease- Positive, Gelatinase- Positive, MR (Methyl Red)- Negative, Urease-Positive, Casein Hydrolysis- Positive, Extracellular electron acceptor |
| 8 | *Achromobacter xylooxidan* (MTCC 25024) | Same microbe as S.No.4 |

In yet another embodiment of the present invention, the nutrient formulation used in Stage-3 comprises $KH_2PO_4$, $K_2HPO_4$, MgSO4, $(NH_4)_2SO_4$, $KNO_3$, peptone, yeast extract, trace element and multi vitamin solution.

In an embodiment of the present invention, Stage 1 and Stage 2 are performed in same reactor. In another embodiment of the present invention, Stage 1 and Stage 2 are performed in different reactor. In yet another embodiment of the present invention, Stage 2 and Stage 3 are performed in different reactors. In yet another embodiment of the present invention, the working chamber with spent caustic of stage-1 can be abiotic or can be added with the selective bacteria for sulfide oxidation to sulfur.

Yet another embodiment of the present invention relates to a method where in stage 2 the oxygen concentration remains less than 7 mg/l.

In yet another embodiment of the present invention, the electrochemical treatment will result in regeneration of caustic at cathode and to increase its pH to 12-14 and decrease the pH of anode to 7-9.

FIG. 3 Represents the Control (Experiment):

In control experiment, the apparatus for stage-1 only is used without any biocatalyst and any further stages of treatment. The apparatus is similar to the other two approaches comprising of two chambers separated by cation exchange membrane (CEM) 1. One chamber is inserted with graphite rod wrapped with activated carbon cloth (ACC) 2 and considered as working chamber where the spent caustic treatment occurs. The electrodes for this chamber can be varied, viz., graphite plate, carbon brush, carbon paper, graphite felt, etc. The other chamber is inserted with graphite electrode wrapped with stainless steel mesh (SS) 3 and considered as counter chamber. The counter chamber may be of any carbon based electrodes coated with noble metals. One chamber having ACC electrode 1 was fed with spent caustic 4, while the other chamber was fed with distilled water 5. The spent caustic chamber as well as counter chamber was maintained under anaerobic conditions. Both the chambers are equipped with Ag/AgCl (3M KCL) reference electrode 6. Both these electrodes will be connected through only external resistance but no power supply 7 given. The spent caustic 4 loaded to the working electrode chamber and distilled water 5 to the counter electrode chamber. As there is no potential gradient created, no cations 8 exchange via the CEM 1 to the counter electrode chamber observed, resulting in no pH alteration observed in both working and counter electrode chambers. There is no caustic 13 regeneration and sulfur 15 recovery as well as treatment of spent caustic, as there is no additional treatment stages available in control operation.

Having described the basic aspects of the present invention, the following non-limiting examples illustrate specific embodiment thereof.

Example 1: Recovery of Caustic from the Spent Caustic

The recovery of caustic from spent caustic is done in stage-1 process where, one of the two chambers is inserted with graphite rod wrapped with ACC and fed with spent caustic, while the counter chamber is inserted with graphite electrode wrapped with SS and fed with distilled water. The electrodes were connected to potentiostat and voltage of +2V against Ag/AgCl reference electrode was applied to the electrode in counter chamber and pH of the counter chamber was monitored at regular time intervals. The current generation from the system started increasing with time and in $2h$ of operation, it reached 15±0.5 A/m2, which sustained afterwards at more or less similar value till 12 h of operation. Within 12 h, the pH of the counter chamber reached to 12.67 and the pH of working chamber reached 12.89 indicating the caustic recovery at the counter chamber. Immediately, the content from counter chamber was replaced with fresh distilled water and the applied potential continued. During this cycle, the current from the cell decreased a bit but sustained at more or less similar value (13±0.84 A/m2) till 4 h of operation followed by a gradual decrement to a lower value by $9^{th}$ h of operation (4.5±1.26 A/m2) and remained at the same value thereafter. During this cycle, the pH of counter chamber again started increasing immediately after start up and reached to 12.04 in 12 h and the associated pH drop of spent caustic is 7.94.

TABLE 1

Change in pH with time in working and counter chambers

|  | Cycle 1 | | Cycle 2 | |
| --- | --- | --- | --- | --- |
| Time (h) | Spent caustic | Distilled water | Spent caustic | Distilled water |
| $0^{th}$ h | 14 | 6.20 | 12.89 | 6.23 |
| $1^{st}$ h | 14 | 6.92 | 12.02 | 7.24 |
| $4^{th}$ h | 13.62 | 8.91 | 10.67 | 9.06 |
| $8^{th}$ h | 13.15 | 10.68 | 8.86 | 11.14 |
| $12^{th}$ h | 12.89 | 12.67 | 7.94 | 12.04 |

Example 2: Simultaneous Recovery of Caustic and Sulfur

The recovery of caustic along with sulfur was attempted by adding selective sulfide oxidizing bacteria to the spent caustic at working chamber of stage-1 bioreactor. One of the two chambers is inserted with graphite rod wrapped with ACC and fed with spent caustic, while the counter chamber is inserted with graphite electrode wrapped with SS and fed with distilled water. Working chamber was inoculated with selectively enriched sulfide oxidizing bacteria (10% v/v). The electrodes were connected to potentiostat and voltage of electrode in working chamber was maintained around −0.3 V (vs Ag/AgCl) by regulating the potential of electrode in counter chamber against Ag/AgCl reference electrode. The applied potential of electrode in counter chamber was adjusted to +1 V initially to maintain the working chamber at −0.3 V but within 1 h, this has come down to +0.8 V due to the start up of biocatalyst function. This was sustained till the end of operation. Change in pH of the counter chamber and the sulfide content of the spent caustic at working chamber was monitored at regular time intervals. The current generation from the system started increasing with time and in 4 h of operation, it reached 5±0.5 A/m2, which sustained afterwards at more or less similar value till 12 h of operation. Within 12 h, the pH of the counter chamber reached to 13.04 and the pH of working chamber reached 12.12 indicating the caustic recovery at the counter chamber. On the other hand, the sulfide content of the spent caustic decreased by 30% in first 12 h. Immediately, the content from counter chamber was replaced with fresh distilled water and the applied potential continued. No significant change in current was observed till 6 h of operation (4.8±0.92 A/m2) followed by a rapid decrement to lower value within 2 h (2.8±1.14 A/m2) and remained more or less similar till the end of operation. During this cycle, the pH of counter chamber again started increasing immediately after start up and reached to 12.68 in 12 h and the associated pH drop of spent caustic is 7.08. (Table-2). Similarly, the sulfide removal reached to about 96% and the sulfur formed during reaction was deposited on the electrode which was measured to be 72±8%. (Table-3)

TABLE 2

Change in pH with time in working and counter chambers

|  | Cycle 1 | | Cycle 2 | |
| --- | --- | --- | --- | --- |
| Time (h) | Spent caustic | Distilled water | Spent caustic | Distilled water |
| $0^{th}$ h | 14 | 6.24 | 12.12 | 6.18 |
| $1^{st}$ h | 14 | 6.52 | 11.06 | 7.45 |
| $4^{th}$ h | 14 | 7.91 | 10.22 | 9.46 |
| $8^{th}$ h | 13.15 | 10.24 | 8.36 | 11.54 |
| $12^{th}$ h | 12.12 | 13.04 | 7.08 | 12.68 |

TABLE 3

Change in sulfide content (% w/v) with time in working and counter chambers

|  | Cycle 1 | | Cycle 2 | |
| --- | --- | --- | --- | --- |
| Time (h) | Sulfide content (% W/v) | Removal (%) | Sulfide content (% W/v) | Removal (%) |
| $0^{th}$ h | 2.52 | 0 | 1.42 | 0 |
| $1^{st}$ h | 2.48 | 1.59 | 1.06 | 57.93 |
| $4^{th}$ h | 2.04 | 19.05 | 0.81 | 67.85 |
| $8^{th}$ h | 1.86 | 26.19 | 0.44 | 82.54 |
| $12^{th}$ h | 1.42 | 43.65 | 0.26 | 96.50 |

Example 3: Biological Conversion of Sulfides to Sulfur

The spent caustic treated in stage-1 was fed in a CSTR with air bubbling system reactor and to the reactor nutrient system containing $K_2HPO_4$ (4 g/l), $KH_2PO_4$ (4 g/l), $MgCl_2$ (0.2 g/l), 0.5 g/l of trace elements, sodium carbonate (2 g/l), yeast extract (5 g/l), sodium nitrate (4 g/l), citrate (5-10 g/l), sorbitol ester (5 ppm), Oleic acid (100 ppm), pantothenic acid (20 ppm), thiamine (25 ppm) was added. The reactor is inoculated with *Thiobacillus* sp. The oxygen concentration of the reactor was maintained to 5 mg/ml initially for 2 hr followed 2 mg/ml level for next two hours. The stirring of the reactor was adjusted at 50 rpm. To prevent the release of volatile compounds from the system, gas phases are continuously recycled. The recycled gas is first passed to a condenser (maintained at 5 degree Celsius) to recover the volatile compounds and metabolites. An control without bacteria was also run under similar conditions. Various sulphur species were analysed according to Chen and Moris 1972 (Environmental Science and Technology Vol 6, No. 6, pp 529-537). The quantitative result showed conversion of more than 70% of sulfides to the elemental sulfur.

Example 4: Removal of the Other Contaminants from Spent Caustic

Treatment of effluent of stage 2 is done in continuously fed CSTR. The spent caustic is fed in the reactor (2 L volume) along with nutrient system consisting of $K_2HPO_4$ (4 g/l), $KH_2PO_4$ (4 g/l), $MgCl_2$ (0.2 g/l), 0.5 g/l of trace elements, sodium carbonate (5 g/l), yeast extract (7 g/l), ammonium nitrate (8 g/l), citrate (8 g/l), sorbitol ester (5 ppm), Oleic acid (230 ppm), pantothenic acid (20 ppm), thiamine (25 ppm). The first reactor (2 L volume) was operated as 40 degree Celsius and incoculated with microbial consortium to obtain the cell count of $>10^2$ CFU/ml and the spent caustic solution was continuously fed with HRT of 24 hrs with percentage of oxygen saturation level was maintained at 100% with stirring of 500 rpm. To prevent the release of VOC from the system, the gas phases were continuously recycled. The recycled gas first passed a condenser to recover VOC and the fed to the same reactor. A control without microbes was run parallel. Un-treated and treated were analyzed for contaminant level using appropriate analytical tools. The results are shown in table-4.

TABLE 4

Treatment of spent caustic in continuous mode

| Contaminant | Content in % | |
|---|---|---|
| | After treatment with microbial blend | Control without microbial blend |
| Mercaptans | 0.01 | 2.86 |
| Phenol | 0.0002 | 0.029 |
| Hydrocarbons | 0.0001 | 0.32 |
| Napthenic acid | 0.0002 | 0.029 |
| Amines | 1.2 | 0.015 |

While specific language has been used to describe the present subject matter, any limitations arising on account thereto, are not intended. As would be apparent to a person in the art, various working modifications may be made to the method in order to implement the inventive concept as taught herein.

Advantages of Invention

1) Environmentally benign, faster and efficient method compared to the existing methods
2) Less energy intensive than existing processes.
3) Regeneration of caustic is possible which can be re-used as such or at least can be used for make-up avoiding the fresh requirement in bulk.
4) Recovery of sulfur in eco-friendly manner which can avoid the additional treatment methods and also the sulfur can be marketed or may be re-used.
5) ETP operation made easy, economic and also helps in meeting the stringent regulations
6) Reduction in overall cost of the treatment process.

We claim:

1. A method for treatment of spent caustic and recovery of caustic and sulphur by bioelectrochemical process, the method comprising:
   (i) treating a spent caustic in an electrochemical reactor comprising two chambers separated by a cation exchange membrane, wherein a first chamber comprises an electrode wrapped with an activated carbon cloth and a second chamber comprises an electrode coated with a noble metal, wherein cations present in the spent caustic are exchanged via the cation exchange membrane from the first chamber to the second chamber causing a pH of about 12-14 in the second chamber and a pH of about 7-9 of the spent caustic in the first chamber;
   (ii) treating the spent caustic from the first chamber using a biocatalyst for anaerobically oxidizing sulfides to obtain a spent caustic stream having an elemental sulphur or its oxidized form, wherein the biocatalyst comprises one or more microbes selected from a group consisting of *Thiobacillus* sp., *Thiomicrospira* sp. and *Pseudomonas putida*; and
   (iii) treating the spent caustic stream obtained from step (ii) using an aerobic biocatalyst to obtain a liquid with reduced concentration of sodium hydroxide, sulfides, amines, thiols, sulphur containing compounds, phenols, hydrocarbons, naphthenic acids and their derivatives, wherein the biocatalyst comprises one or more of *Pseudomonas putida* (MTCC 5385), *Pseudomonas aeruginosa* IOCX (MTCC 5389), *Bacillus* substilis (MTCC 5386), *Achromobacter xylosoxidan* IOC-SC-4 (MTCC 25024), *Pseudomonas stutzeri* (MTCC 25027), *Arthrobacter* sp. (MTCC 25028), *Bacillus subtilis* (MTCC 25026), and *Achromobacter* xylooxidan (MTCC 25024).

2. The method as claimed in claim 1, wherein the microbes in the biocatalyst of step (ii) are used in an adsorbed form or a free form or immobilized on synthetic plastics, surface-modified carbon nanotubes, poly (tetrafluoroethylene) (PTFE) fibrils, a zeolite, a clay, an anthracite, a porous glass, an activated charcoal, ceramics, an acrylamide, polyurethane, polyvinyl, resins or a natural polymer.

3. The method as claimed in claim 1, wherein the pH in the second chamber is 12.68 and the pH of spent caustic in the first chamber is 7.08 in 12 hours.

4. The method as claimed in claim 1, wherein anaerobically oxidizing sulfides comprises anaerobically oxidizing about 96% of sulfides and wherein obtaining the spent caustic stream having an elemental sulphur comprises obtaining the spent caustic stream having 72±8% of sulphur.

5. A method for treatment of spent caustic and recovery of caustic and sulphur by bioelectrochemical process, the method comprising:
   (i) treating a spent caustic in an electrochemical reactor comprising two chambers separated by a cation exchange membrane, wherein a first chamber comprises an electrode wrapped with an activated carbon cloth and a biocatalyst present as biofilm on the electrode and a second chamber comprises an electrode coated with a noble metal, wherein cations present in the spent caustic are exchanged via the cation exchange membrane from the first chamber to the second chamber causing a pH of about 12-14 in the second chamber and a pH of about 7-9 of the spent caustic in the first chamber;
   wherein the biocatalyst present as a biofilm anaerobically oxidizes sulfides to obtain a spent caustic stream having an elemental sulphur or its oxidized form, wherein the biocatalyst comprises one or more microbes selected from a group consisting of *Thiobacillus* sp., *Thiomicrospira* sp. and *Pseudomonas putida*; and
   (ii) treating the spent caustic stream obtained from step (i) using an aerobic biocatalyst to obtain a liquid with reduced concentration of sodium hydroxide, sulfides, amines, thiols, sulphur containing compounds, phenols, hydrocarbons, naphthenic acids and their derivatives, wherein the biocatalyst comprises one or more of *Pseudomonas putida* (MTCC 5385), *Pseudomonas aeruginosa* IOCX (MTCC 5389), *Bacillus* substilis (MTCC 5386), *Achromobacter* xylosoxidan IOC-SC-4 (MTCC 25024) *Pseudomonas stutzeri* (MTCC 25027), *Arthrobacter* sp. (MTCC 25028), *Bacillus subtilis* (MTCC 25026), and *Achromobacter* xylooxidan (MTCC 25024).

6. The method as claimed in claim 5, wherein the pH in the second chamber is 12.68 and the pH of spent caustic in the first chamber is 7.08 in 12 hours.

7. The method as claimed in claim 5, wherein anaerobically oxidizing sulfides comprises anaerobically oxidizing about 96% of sulfides and wherein obtaining the spent caustic stream having an elemental sulphur comprises obtaining the spent caustic stream having 72±8% of sulphur.

8. A system for treatment of spent caustic to recover caustic and sulphur, the system comprising:
   (i) an apparatus for stage 1 comprising two chambers separated by a cation exchange membrane,
      a first chamber receiving spent caustic comprises an electrode wrapped with an activated carbon cloth, a reference electrode and connected to a power supply;
      a second chamber receiving distilled water comprises an electrode coated with a noble metal, a reference electrode and connected to a power supply;
      the first chamber and the second chamber are maintained at anaerobic condition, wherein cations present in the spent caustic are exchanged via the cation exchange membrane from the first chamber to the second chamber causing a pH of 12-14 in the second chamber and a pH of 7-9 of spent caustic at anode in the first chamber, wherein caustic is regenerated and recovered in the second chamber;
   (ii) an apparatus for stage 2 comprises a biocatalyst, wherein said apparatus receives the spent caustic stream from first chamber with lowered pH from stage 1 and anaerobically oxidizes sulfides to obtain a spent caustic stream having an elemental sulfur or its oxidized form by using biocatalyst and recovers sulphur, wherein the biocatalyst comprises one or more microbes selected from group consisting of *Thiobacillus* sp., *Thiomicrospira* sp. and *Pseudomonas putida*; and
   (iii) a reactor for stage 3 comprises aerobic biocatalyst, wherein said apparatus receives spent caustic stream from stage 2 for treatment by the aerobic biocatalyst and discharges completely treated liquid with reduced concentration of sodium hydroxide, sulfides, amines, thiols, sulphur containing compounds, phenols, hydrocarbons, naphthenic acids and their derivatives, wherein the biocatalyst comprises one or more of *Pseudomonas putida* (MTCC 5385), *Pseudomonas aeruginosa* IOCX (MTCC 5389), *Bacillus* substilis (MTCC 5386), *Achromobacter* xylosoxidan IOC-SC-4 (MTCC 25024) *Pseudomonas stutzeri* (MTCC 25027), *Arthrobacter* sp. (MTCC 25028), *Bacillus subtilis* (MTCC 25026), and *Achromobacter* xylooxidan (MTCC 25024).

9. The system as claimed in claim 8, wherein stage 2 is combined with stage 1 and the biocatalyst of stage 2 is present as biofilm on the electrode in the first chamber of stage 1,
   wherein the spent caustic is treated with the biocatalyst for anaerobically oxidizing the sulfides to obtain a spent caustic having an elemental sulfur or its oxidized form and recovering sulphur; and
   wherein the spent caustic stream is fed to subsequent stage reactor comprising aerobic biocatalyst for treating the spent caustic stream and discharging completely treated liquid with reduced concentration of sodium hydroxide, sulfides, amines, thiols, sulphur containing compounds, phenols, hydrocarbons, naphthenic acids and their derivatives.

10. The system as claimed in claim 8, wherein in stage 1, the electrode in the first chamber comprises graphite rod, graphite plate, carbon brush, carbon paper, graphite felt; and the electrode in the second chamber comprises a carbon based electrode coated with noble metals, preferably graphite electrode wrapped with stainless steel mesh.

11. The system as claimed in claim 8, wherein the apparatus for stage 2 is configured to anaerobically oxidize about 96% of sulfides and recover 72±8% of sulphur.

12. The system as claimed in claim 9, wherein in stage 1, the electrode in the first chamber comprises graphite rod, graphite plate, carbon brush, carbon paper, graphite felt; and the electrode in the second chamber comprises a carbon based electrode coated with noble metals, preferably graphite electrode wrapped with stainless steel mesh.

13. The system as claimed in claim 9, wherein the apparatus for stage 1 is configured to anaerobically oxidize about 96% of sulfides and recover 72±8% of sulphur.

14. The method as claimed in claim 5, wherein the microbes in the biocatalyst of step (i) are used in an adsorbed form or a free form or immobilized on synthetic plastics, surface-modified carbon nanotubes, poly (tetrafluoroethylene) (PTFE) fibrils, a zeolite, a clay, an anthracite, a porous glass, an activated charcoal, ceramics, an acrylamide, polyurethane, polyvinyl, resins or a natural polymer.

* * * * *